United States Patent
Harris et al.

(10) Patent No.: US 9,717,494 B2
(45) Date of Patent: Aug. 1, 2017

(54) APPLIER FOR ANCHORING A LINING TO A HOLLOW ORGAN

(75) Inventors: Jason L. Harris, Lebanon, OH (US); Alessandro Pastorelli, Rome (IT); Michele D'Arcangelo, Rome (IT); Mark S. Ortiz, Milford, OH (US); Mark S. Zeiner, Mason, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 233 days.

(21) Appl. No.: 14/364,452

(22) PCT Filed: Dec. 13, 2011

(86) PCT No.: PCT/EP2011/072579
§ 371 (c)(1),
(2), (4) Date: Jun. 11, 2014

(87) PCT Pub. No.: WO2013/087095
PCT Pub. Date: Jun. 20, 2013

(65) Prior Publication Data
US 2015/0038987 A1    Feb. 5, 2015

(51) Int. Cl.
*A61B 17/04* (2006.01)
*A61B 17/11* (2006.01)
*A61B 17/30* (2006.01)

(52) U.S. Cl.
CPC ...... *A61B 17/0491* (2013.01); *A61B 17/0469* (2013.01); *A61B 2017/1142* (2013.01); *A61B 2017/306* (2013.01)

(58) Field of Classification Search
CPC . A61B 17/0469; A61B 17/0491; A61B 17/04; A61B 17/0482; A61B 17/0483
See application file for complete search history.

(56) References Cited

U.S. PATENT DOCUMENTS

| | | | | |
|---|---|---|---|---|
| 5,037,021 A | * | 8/1991 | Mills | A61B 17/0469 227/175.1 |
| 5,766,186 A | * | 6/1998 | Faraz | A61B 17/0469 606/145 |
| 5,792,153 A | * | 8/1998 | Swain | A61B 17/0469 112/169 |
| 5,891,159 A | | 4/1999 | Sherman et al. | |
| 5,911,727 A | * | 6/1999 | Taylor | A61B 17/0491 606/139 |
| 5,947,983 A | * | 9/1999 | Solar | A61B 17/0469 604/22 |

(Continued)

FOREIGN PATENT DOCUMENTS

EP    1749482 A2    2/2007
GB    2200072 A    7/1988

*Primary Examiner* — Christopher L Templeton
(74) *Attorney, Agent, or Firm* — Mintz Levin Cohn Ferris Glovsky and Popeo, P.C.

(57) ABSTRACT

Provided herein are medical apparatuses and methods and more particularly devices and methods for positioning and anchoring a lining to a hollow body organ, such as a stomach, intestine or gastrointestinal tract. For example, in one embodiment, an endoluminal applier includes a fastening assembly configured to receive tissue and lining, a suction device configured to acquire tissue and lining, and a stitching mechanism configured to stitch into the fastening cavity and to apply a running suture to the tissue portion and lining.

9 Claims, 9 Drawing Sheets

(56) References Cited

U.S. PATENT DOCUMENTS

| | | | |
|---|---|---|---|
| 6,443,962 B1* | 9/2002 | Gaber | A61B 17/0491 112/80.04 |
| 6,719,764 B1* | 4/2004 | Gellman | A61B 17/0469 606/144 |
| 7,993,354 B1* | 8/2011 | Brecher | A61B 17/0482 606/145 |
| 2002/0193809 A1* | 12/2002 | Meade | A61B 17/0469 606/144 |
| 2003/0045891 A1 | 3/2003 | Yamamoto et al. | |
| 2003/0208209 A1* | 11/2003 | Gambale | A61B 17/00234 606/144 |
| 2005/0015101 A1* | 1/2005 | Gibbens, III | A61B 17/0482 606/144 |
| 2006/0047289 A1* | 3/2006 | Fogel | A61B 17/0469 606/139 |
| 2006/0069396 A1* | 3/2006 | Meade | A61B 17/0482 606/144 |
| 2006/0224184 A1* | 10/2006 | Stefanchik | A61B 17/0482 606/222 |
| 2006/0282089 A1* | 12/2006 | Stokes | A61B 1/00087 606/144 |
| 2006/0282098 A1* | 12/2006 | Shelton | A61B 1/00087 606/144 |
| 2007/0129735 A1* | 6/2007 | Filipi | A61B 17/0469 606/144 |
| 2008/0071295 A1* | 3/2008 | Baxter | A61B 17/0469 606/144 |
| 2009/0209980 A1* | 8/2009 | Harris | A61B 17/0491 606/144 |
| 2010/0160934 A1 | 6/2010 | Kelleher et al. | |
| 2013/0178854 A1* | 7/2013 | Sholev | A61B 17/0469 606/79 |

\* cited by examiner

APPLIER FOR ANCHORING A LINING TO A HOLLOW ORGAN

RELATED APPLICATIONS

This application is a national stage application, filed under 35 U.S.C. §371, of International Application No. PCT/EP2011/072579 filed on Dec. 13, 2011, the contents which are hereby incorporated by reference in its entirety.

FIELD OF THE INVENTION

The present invention relates generally to medical apparatuses and methods and more particularly to devices and methods for positioning and anchoring a lining to a hollow body organ, such as a stomach, intestine or gastrointestinal tract.

BACKGROUND OF THE INVENTION

In cases of severe obesity, patients may currently undergo several types of surgery either to tie off or staple portions of the large or small intestine or stomach, and/or to bypass portions of the same to reduce the amount of food desired by the patient, and the amount absorbed by the gastrointestinal tract. The procedures currently available include laparoscopic banding, where a device is used to "tie off" or constrict a portion of the stomach, vertical banded gastroplasty (VBG), or a more invasive surgical procedure known as a Roux-En-Y gastric bypass to effect permanent surgical reduction of the stomach's volume and subsequent bypass of the intestine.

Although the outcome of these stomach reduction surgeries leads to patient weight loss because patients are physically forced to eat less due to the reduced size of their stomach, several limitations exist due to the invasiveness of the procedures, including time, general anesthesia, healing of the incisions and other complications attendant to major surgery. In addition, these procedures are only available to severely obese patients (morbid obesity, Body Mass Index >=40) due to their complications, including the risk of death, leaving patients who are considered obese or moderately obese with few, if any, interventional options.

In addition to the above described gastrointestinal reduction surgery, endoluminal sleeves are known for partially or totally lining certain portions of the stomach and of the intestine with the aim to separate or bypass at least part of the food flow from the lined portions of the gastrointestinal tract. It has been observed that by creating a physical barrier between the ingested food and certain regions of the gastrointestinal wall by means of endoluminal sleeves, similar benefits for weight loss and improvement or resolution of type 2 diabetes may be achieved as with gastric bypass surgery. Physicians believe that by creating a physical barrier between the ingested food and selected regions of the gastrointestinal wall, it might be possible to purposefully influence the mechanism of hormonal signal activation originating from the intestine.

A known type of endoluminal sleeve relies on metallic expandable structures, such as a stent, to engage the surrounding hollow organ for holding the sleeve in the planned position. To improve anchoring and stability of the sleeve, it is further known to provide the stent with barbs which penetrate the surrounding tissue.

This notwithstanding, it has been observed that the endoscopic sleeves tend to move inside the GI tract and migrate away from their initially planned position.

U.S. Pat. No. 7,220,237 B2, Method and device for use in endoscopic organ procedures, to Gannoe et al. describes procedures for internally lining portions of the gastrointestinal tract, using tubular endoluminal sleeves and stapling devices for circumferentially acquiring tissue of the gastric wall and fixating a circular section of the acquired tissue to which an endoluminal sleeve is secured by shape interference.

However, the known methods and devices for placing and securing endoluminal linings within hollow organs, particularly within the gastrointestinal tract, are not yet satisfactory with regard to a reliable anchoring and conservation of the planned position of the endoluminal sleeve.

Moreover, the known devices and methods do not sufficiently address the need of creating sealed or leak tight connection regions between the endoluminal sleeve and the hollow organ in order to obtain a desired flow scheme of the food flow and the flow of bodily fluids, such as gastric juices, bile and pancreatic fluid.

Accordingly, there is a need for improved devices and procedures for positioning and anchoring an endoluminal sleeve in the GI tract.

SUMMARY OF THE INVENTION

The present invention provides for an improved apparatus and method for the transoral, or endoscopic, positioning and anchoring of an endoluminal lining within a hollow body organ, particularly the gastrointestinal tract, including, but not limited to, the esophagus, stomach, portions of or the entire length of the intestinal tract, etc., unless specified otherwise. In the case of the present invention, the surgeon or endoscopist may insert devices as described below through the patient's mouth, down the esophagus and into the stomach or intestine as appropriate. The procedure can be performed entirely from within the patient's stomach or other intestinal tract, and does not necessarily require any external incision.

At least part of the above identified needs are met by an endoluminal applier for anchoring a tubular lining to a hollow organ, the applier comprising a fastening assembly having:

- a fastening cavity adapted to receive a tissue portion of said hollow organ together with a portion of said lining,
- a suction device with one or more suction apertures opening into the fastening cavity and adapted to acquire the tissue portion and lining into the fastening cavity,
- a stitching mechanism adapted to stitch into said fastening cavity and to apply a running suture to the acquired tissue portion and lining.

This provides an instrumentation which may be used similarly to known circular staplers, but obviates the use of rigid staples and reduces the stiffness of the sutured seam with respect to fastening procedures with staplers. Moreover, the stitching force necessary to pierce a single perforating needle through the acquired tissue and lining is significantly lower than the forces normally required for stapling.

In accordance with an aspect of the invention, the fastening cavity has a first sewing surface defining a first slot extending along a stitching path and an opposite second sewing surface facing the first sewing surface and defining a second slot extending along the stitching path, and the stitching mechanism comprises a perforating needle arranged in the first slot, a thread catch arranged in the second slot, and a needle driving assembly adapted to:

repeatedly moving the perforating needle and the thread catch with respect to each other to create a running suture through said fastening cavity, and moving the perforating needle and the thread catch along the first and second slots to extend the running suture along the stitching path.

In accordance with a further aspect of the invention, the stitching mechanism comprises:

a continuous annular needle path, said needle path crossing the fastening cavity and being formed inside an unobstructed disentangling space;

a needle and needle drive assembly arranged for movement of the needle along the needle path;

a suture secured to the needle and extending from the needle through the disentangling space and through the fastening cavity outside the fastening assembly, so that the needle can repeatedly move along the entire needle path without winding the suture around any part of the fastening assembly.

This allows to position the applier with the fastening cavity over a portion of tissue and lining, acquire the tissue portion and lining in the fastening cavity, sending the needle with the suture through the acquired tissue portion and lining, releasing the tissue portion and lining from the fastening cavity, rotating or moving the fastening cavity to the next portion of tissue and lining and moving the needle along the annular needle path to an initial needle position (without tangling the suture), and repeating the sequence until a complete running suture, e.g. a circumferential purse string suture, is created.

In accordance with a yet further aspect of the invention, the fastening assembly forms a plurality of fastening cavities arranged along a circumference of the fastening assembly, as well as a continuous annular needle path which crosses all fastening cavities and which extends inside a continuously radially externally open annular sewing groove formed along the circumference of the fastening assembly. The stitching mechanism comprises a needle and needle drive assembly arranged for movement of the needle along the needle path, as well as a suture secured to the needle and extending from the needle inside the annular sewing groove, so that the needle can repeatedly move along the entire needle path and the thus obtained suture loop can be moved radially out of the sewing groove.

This embodiment allows to contemporaneously acquire a plurality of tissue portions and lining portions along a circumference around the fastening assembly, then sending the needle successively through all acquired tissue and lining portions, thereby obtaining a (possibly closed loop) running purse string suture between the lining and the tissue of the hollow organ, and eventually releasing the purse string sutured tissue and lining from the applier.

These and other aspects and advantages of the present invention shall be made apparent from the accompanying drawings and the description thereof, which illustrate embodiments of the invention and, together with the general description of the invention given above, and the detailed description of the embodiments given below, serve to explain the principles of the present invention.

DETAILED DESCRIPTION OF EMBODIMENTS

Figure 1:
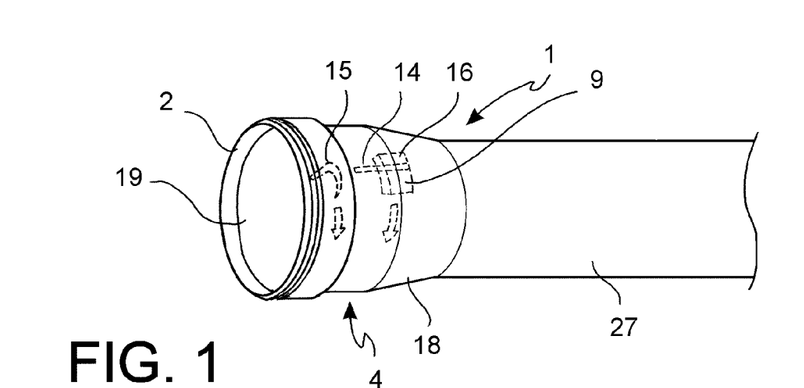
FIG. 1 illustrates an endoluminal applier for anchoring a tubular lining to a hollow organ, the applier being in a closed configuration.
Figures 2, 3:
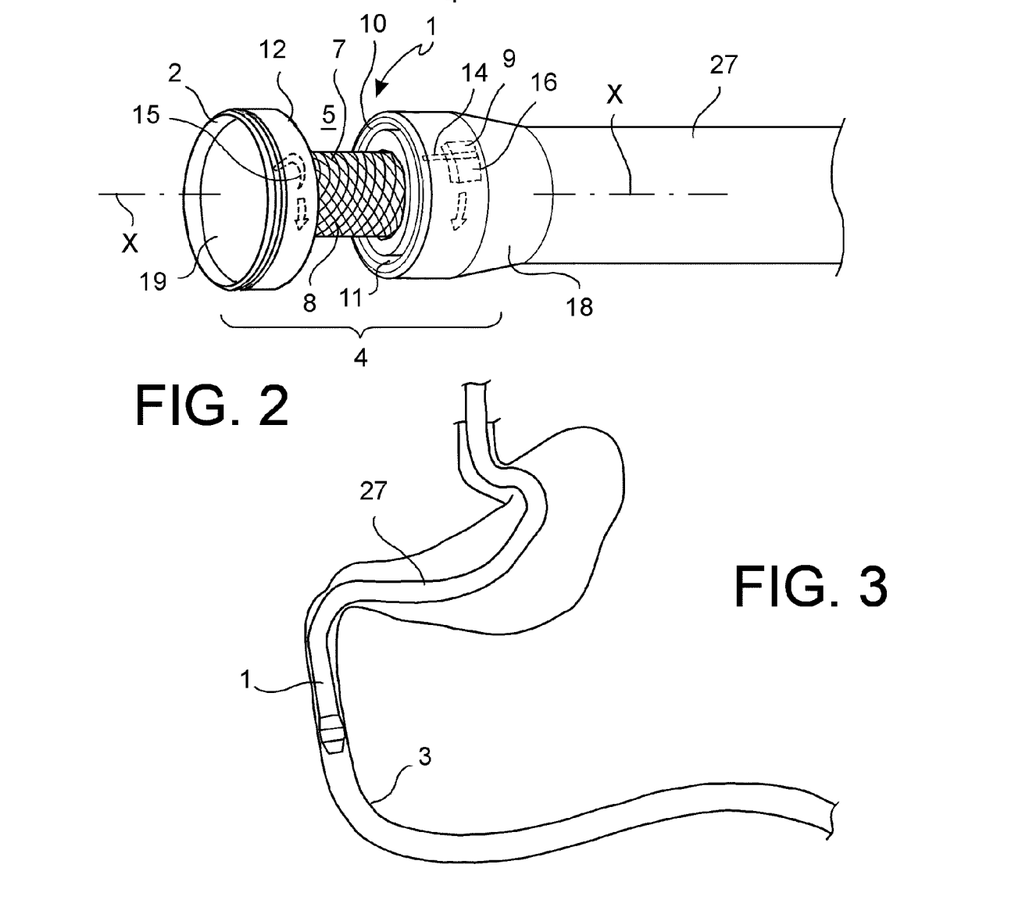
FIG. 2 illustrates the applier of FIG. 1 in an open configuration.
FIG. 3 illustrates a transoral introduction of the applier of FIG. 1 to the duodenum.
Figure 4:
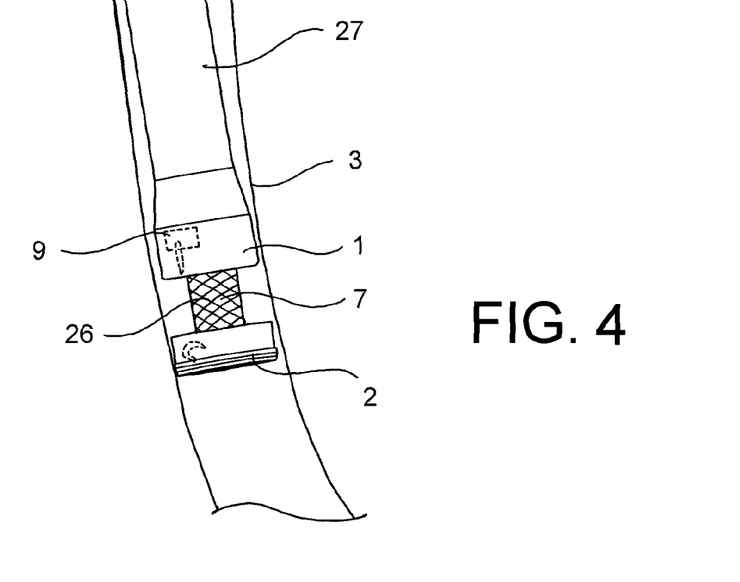
FIG. 4 illustrates a method step in which the applier is opened after positioning in the target location in the GI tract.
Figure 5:
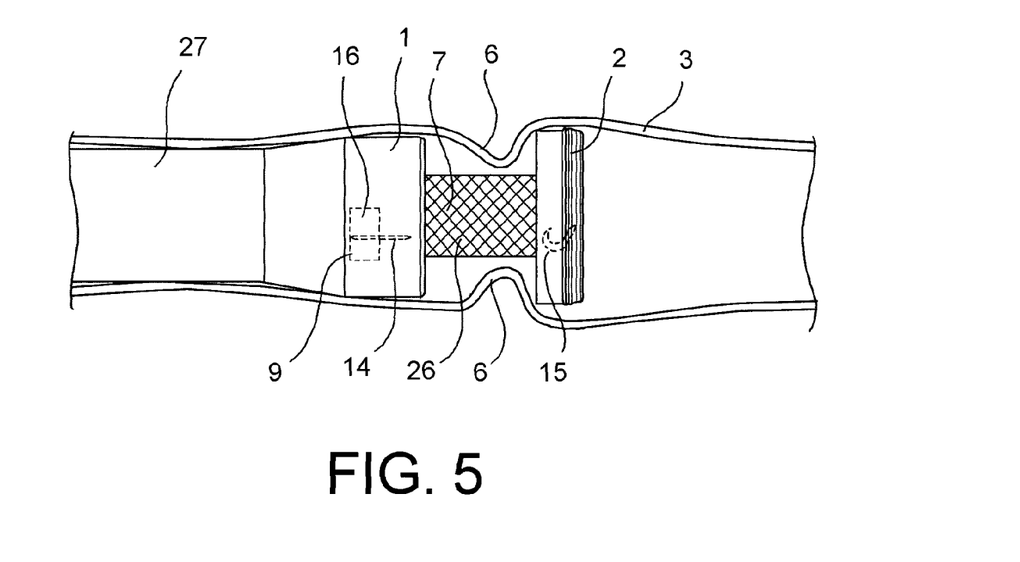
FIG. 5 illustrates the applier and a method for acquiring tissue of the hollow organ to which the tubular lining is intended to be secured in accordance with an embodiment.
Figure 6:
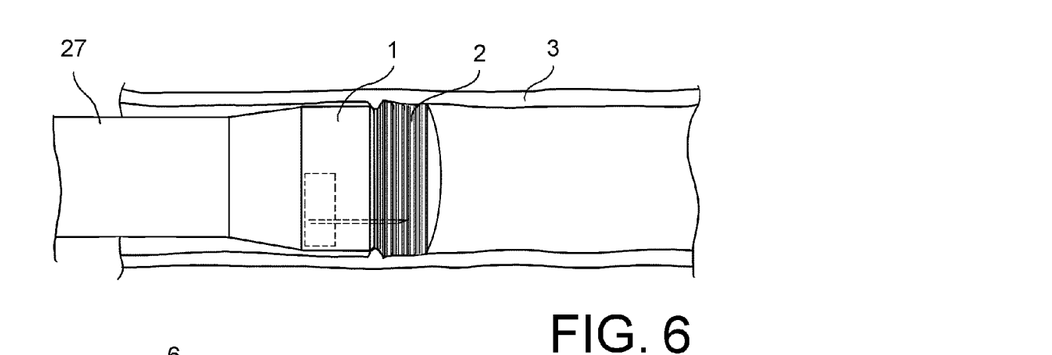
FIG. 6 illustrates the applier in a closed configuration in which the acquired tissue and an anchoring portion of the lining is clamped between opposite sewing surfaces of a fastening cavity of the applier and ready for the application of a running suture.
Figure 7:
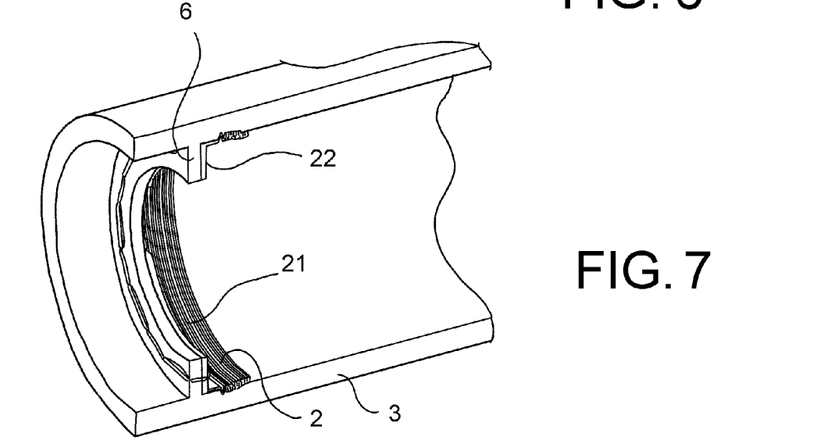
FIG. 7 is a schematic cross-sectional view of a tubular lining sutured to a target location of the hollow organ, but still in a collapsed or packed shape.
Figure 8:
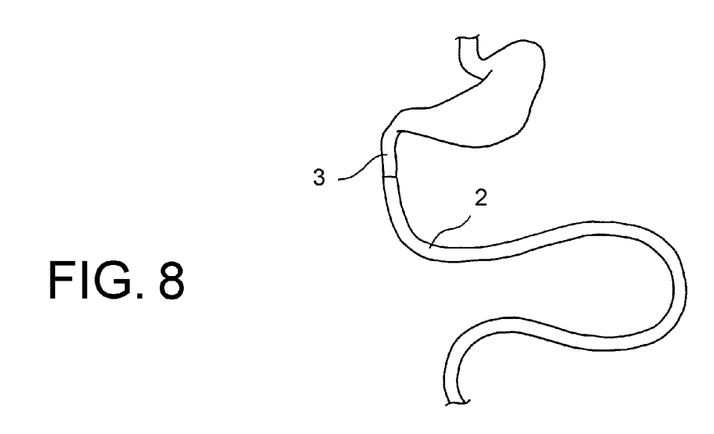
FIG. 8 illustrates the tubular lining after anchoring and full extension within a section of the GI tract.
Figure 9:
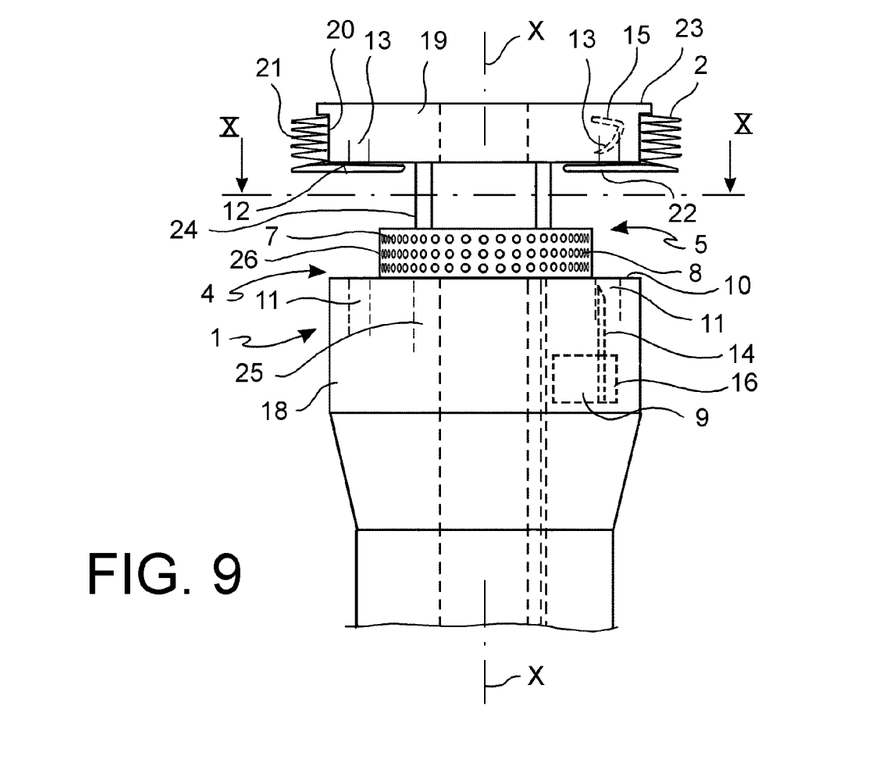
FIG. 9 is a partially sectioned side view of the applier in accordance with a further embodiment.
Figure 10:
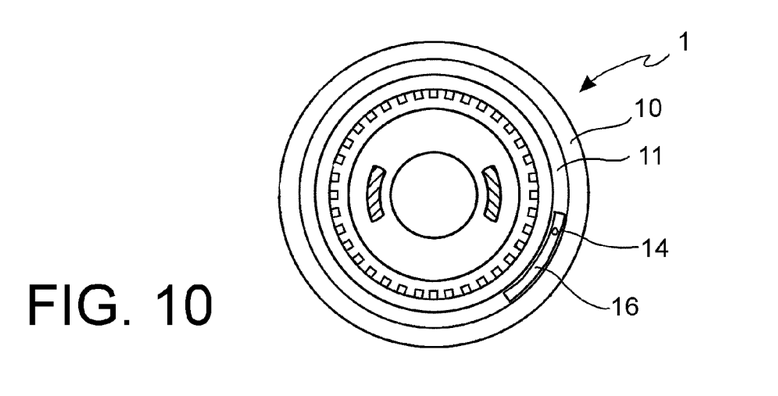
FIG. 10 is sectional view in plane X-X in FIG. 9.
Figures 11A, 11B, 11C, 11D, 11E:
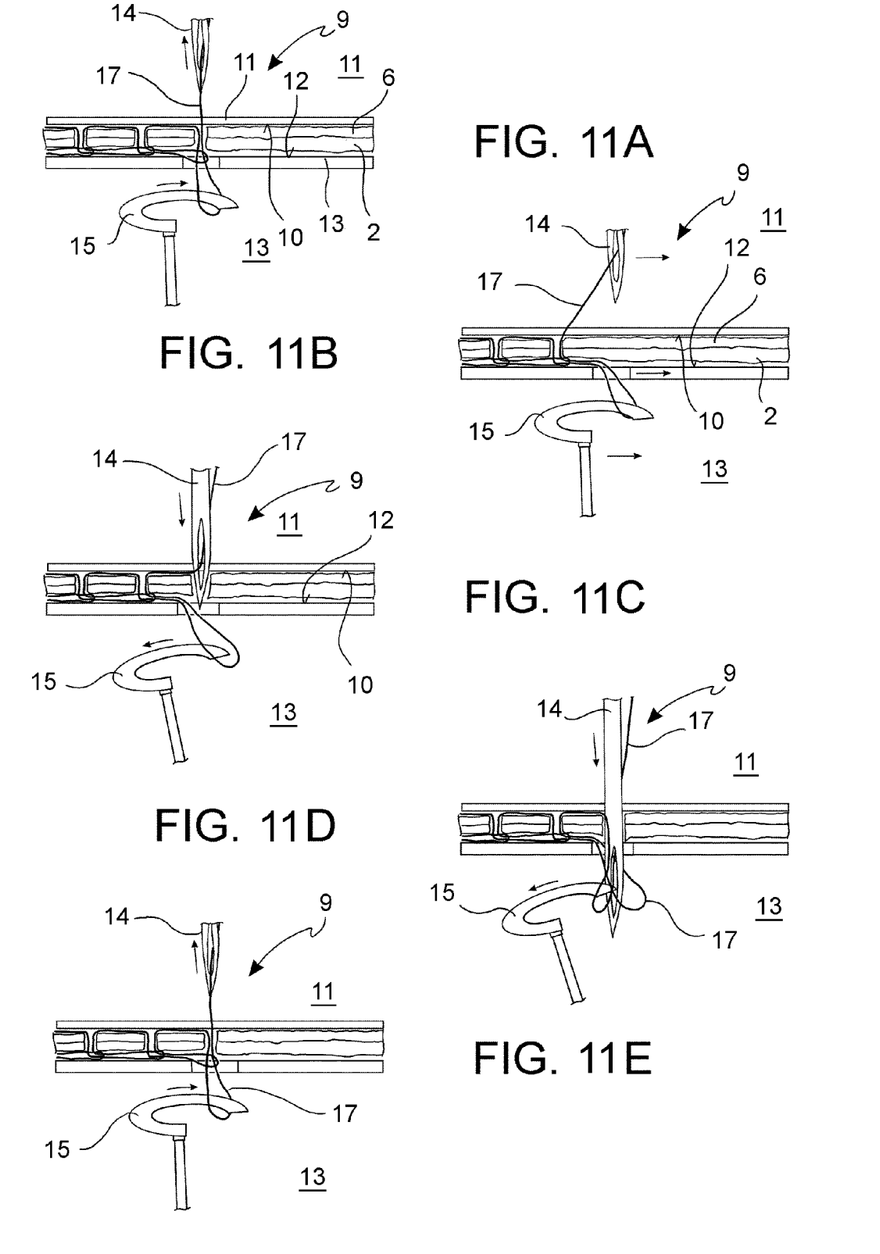
FIGS. 11A through 11E illustrate a sequence of movements accomplished by a stitching mechanism of the applier in accordance with an embodiment.

Referring to the drawings where like numerals denote like anatomical structures and components throughout the several views, FIG. 1 depicts an endoluminal applier 1 for anchoring a tubular lining 2 to a hollow organ 3, particularly to a section of the GI tract of a patient.

The applier 1 comprises a fastening assembly 4 which has a fastening cavity 5 adapted to receive a tissue portion 6 of the hollow organ 3 together with a portion of the lining 2, a suction device 7 with one or more suction apertures 8 opening into the fastening cavity 5 and adapted to acquire the tissue portion 6 and lining 3 into the fastening cavity 5. The fastening assembly 4 further comprises a stitching mechanism 9 adapted to stitch into the fastening cavity 5 and to apply a running suture to the acquired tissue portion 6 and lining 2.

In accordance with an embodiment, the fastening cavity 5 has a first sewing surface 10 defining a first sewing slot 11 extending along a stitching path and an opposite second sewing surface 12 facing the first sewing surface 10 and defining a second sewing slot 13 extending along the stitching path. The stitching mechanism 9 comprises a perforating needle 14 arranged in the first sewing slot 11, a thread catch 15 arranged in the second sewing slot 13, and a needle driving assembly 16. The needle driving assembly 16 is adapted to repeatedly moving the perforating needle 14 and the thread catch 15 with respect to each other to create a running suture through the fastening cavity 5, and to moving the perforating needle 14 and the thread catch 15 along the first and second sewing slots 11, 13 in a manner to extend the running suture along the stitching path.

More specifically, the needle driving assembly 16 can be adapted to repeatedly moving the perforating needle 14 with a suture loop forward through the fastening cavity 5 into the second sewing slot 13 and then backward in the first sewing slot 11, and repeatedly moving the thread catch 15 in engagement with the suture loop 17 to hold the suture loop in the second sewing slot 13 during the backward movement of the perforating needle 14, and moving the perforating needle 14 and the thread catch 15 along the stitching path with respect to the first and second sewing surfaces 10, 12 while the suction device 7 or clamping means which will be described further below constrain the tissue portion 6 and the lining 2 stationarily within the fastening cavity 5.

FIGS. 11A to 11E illustrate an exemplary embodiment of a movement sequence of the stitching mechanism 9, in which a basic chain stitch is created through the lining 2 and tissue portion 6 by first sending the perforating needle 14 forward through the tissue portion and lining held between the first and second sewing surfaces 10, 12. Then, as the perforating needle 14 is moved backward, the friction of the suture 17 against the tissue 6 and lining 2 is sufficient to form a small loop on their side facing the second sewing slot 13. That loop is caught by the hook shaped thread catch 15 housed within the second sewing slot 13. The needle driving assembly 16 then moves both the perforating needle 14 and the thread catch 15 forward along the stitching path, thereby projecting the previously caught loop of suture in the position of the subsequent stitch. In this manner, the next forward movement of the perforating needle 14 goes through the previously caught loop of suture. The thread catch 15 then releases the previously caught loop of suture and picks up the new loop and the process repeats.

In accordance with an embodiment (FIGS. 1 through 10), the fastening assembly 4 comprises a proximal portion 18 having an annular distal clamping surface which forms the first sewing surface 10, and a distal anvil 19 having an annular proximal clamping surface which faces the distal clamping surface and forms the second sewing surface 12. The anvil 19 is movable relative to the proximal portion 18 for clamping a ring shaped tissue portion 6 between the first and second sewing surfaces 10, 12. In this embodiment, the stitching path and, hence, the sewing slots 11, 13 have a closed annular, preferably circular shape.

The fastening assembly 4 may further comprise a ring shaped lining seat 20 adapted to receive the tubular lining 2 such that an elongate body portion 21 of the lining is held in a collapsed (substantially ring shaped), e.g. wrapped, folded, compressed or rolled up, configuration with regard to a lining longitudinal extension and a ring shaped anchoring portion 22 of the lining 2 is held to overlap one of said first and second sewing surfaces 10, 12 and sewing slots 11, 12.

This assures a correct relative positioning of the lining 2 anchoring portion 22, the stitching mechanism 9 and the sewing surfaces 10, 12. Moreover, the positioning of the lining 2 on the lining seat 20 may take place extracorporeally and does not change during the endoluminal insertion of the applier 1 and during applying the running suture.

In accordance with an embodiment, the lining seat 20 is formed in the anvil 19 and comprises a distal containment wall 23 (FIG. 9) against which the collapsed and "packed" tubular lining 2, e.g. an endoluminal sleeve, rests so that it keeps its collapsed and "packed" shape until the lining 2 is pulled or pushed distally over the containment wall 23 during withdrawal of the applier 1 from the sutured sleeve 2.

The anvil 19 may be translatably connected to the proximal portion 18 by at least one, preferably two diametrically opposite anvil shafts 24 slidably received in one or more guide holes 25 of the proximal portion 18 and connected with an anvil moving mechanism adapted to move the anvil 19 relative to the proximal portion 18.

The suction apertures 8 of the suction device 7 are connectable to an extracorporeal suction pump and may be arranged in the fastening cavity 5 radially internal of the sewing slots 11, 13 in a manner to assure an acquisition and positioning of the tissue and lining over the sewing slots.

The suction apertures 8 can be formed in the first sewing surface 10 and/or in the region of the anvil shaft or shafts 24. Suction apertures 8 may be also formed in a radially external surface of a ring shaped suction wall 26 provided in the fastening cavity 5 radially inside with respect to the sewing slots 11, 13.

The anvil moving mechanism is connected through one or more flexible anvil movement transmitters with an extracorporeal anvil movement activation mechanism provided e.g. at a proximal handle portion of the applier 1. The stitching mechanism 9 can be mechanically activated by flexible rotation transmitters or it can be electrically energized by flexible electric cables. Both the anvil movement transmitters and the stitching movement transmitters or electric cables are arranged inside the flexible shaft 27 of the applier 1.

In accordance with a further embodiment (FIGS. 12 through 15), the fastening assembly 4 forms a continuous annular needle path 28 which crosses the fastening cavity 5 and which is formed inside an unobstructed disentangling space 29 defined inside the fastening assembly 4, and the stitching mechanism 9 comprises a needle 30 and needle drive assembly 31 arranged for movement of the needle 30 along the needle path 28. A suture 17 is secured to the needle 30 and extends from the needle 30 through the disentangling space 29 and through the fastening cavity 5 outside the fastening assembly 4, so that the needle 30 can repeatedly move along the entire needle path 28 (with the attached suture thread 17 repeatedly forming and disentangling open loops, compare FIG. 13A, and) without winding the suture 17 around any part of the fastening assembly 4.

A thus configured applier allows a sequential acquisition and suturing of a plurality tissue and lining portions along a circumference of the hollow organ by a single continuous suture thread, thereby creating a purse string suture which secures the lining 2 to the wall of the hollow organ, particularly of a section of GI tract.

Figures 15, 16, 17, 18:
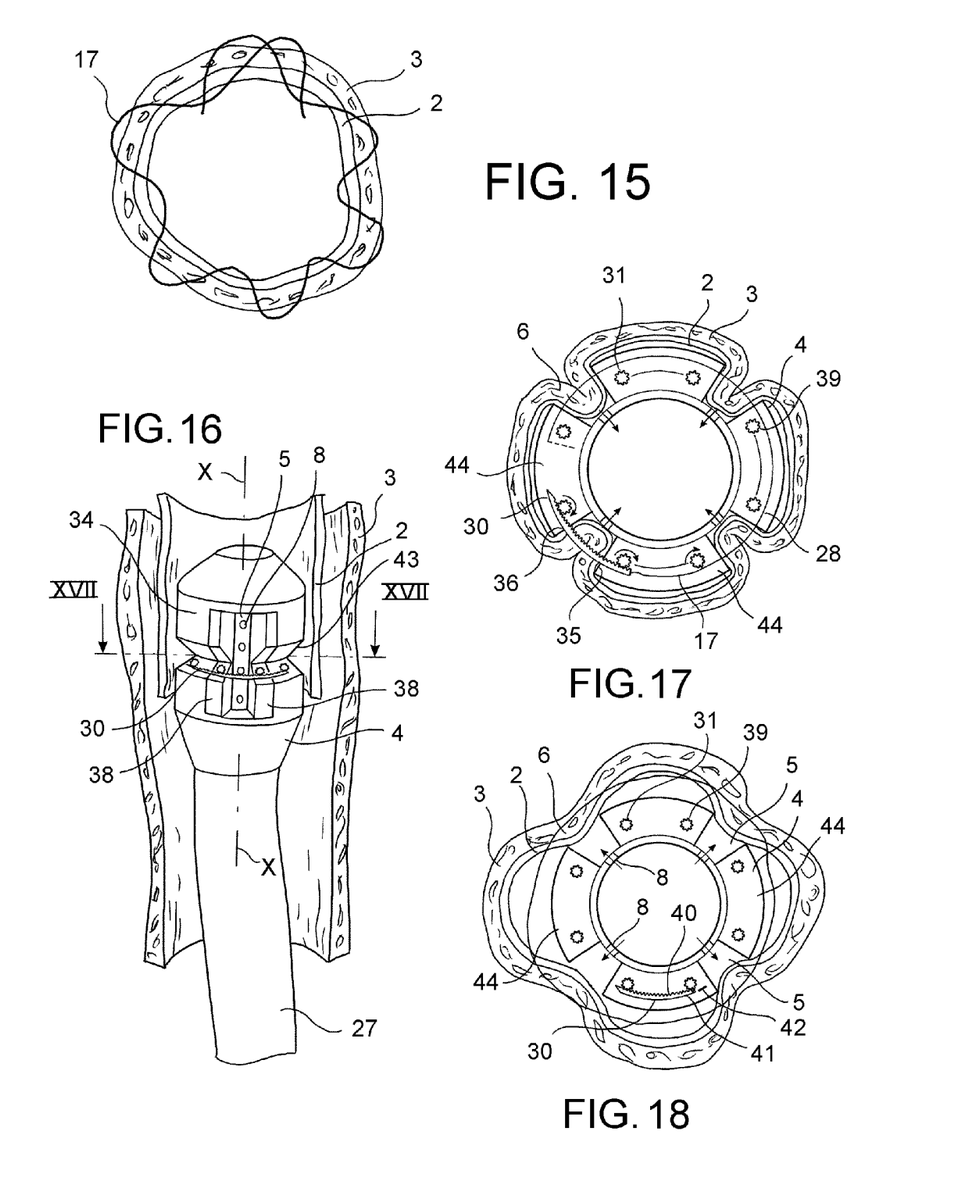
FIG. 15 is a sectional view of a purse string suture through an endoluminal lining and an intestinal wall created by means of the applier in FIG. 12.
FIG. 16 illustrates an endoluminal applier for securing a tubular lining to a hollow organ in accordance with a further embodiment.
FIG. 17 is sectional view in plane XVII-XVII in FIG. 16 during a suturing step.
FIG. 18 is sectional view in plane XVII-XVII in FIG. 16 during a tissue releasing step.

Specifically, the applier 1 can be positioned with the fastening cavity 5 over a portion of tissue 6 and lining 2, acquire the tissue portion 6 and lining 2 in the fastening cavity (by suction), sending the needle 30 with the suture 17 through the acquired tissue portion and lining, then releasing the tissue portion and lining from the fastening cavity 5, rotating or moving the fastening cavity 5 to the next portion of tissue and lining and moving the needle 30 along the annular needle path 28 to an initial needle position (without entangling the suture 17, compare FIG. 13A), and repeating the same sequence until a complete running suture, e.g. a circumferential purse string suture, is created (FIG. 15).

In order to facilitate a rotation of the fastening assembly 4 to a subsequent tissue portion and lining region and, at the same time, enable a suture feeding to and through the previously sutured portions of tissue and lining, the fastening assembly 4 may comprise an externally continuously open annular suture feeding channel 32 which extends all around the fastening assembly 4 and which is adapted for feeding the suture 17 from any point along the suture feeding channel 32.

For this purpose, a reel 33 of suture 17 may be arranged inside the suture feeding channel 32 and adapted to slide along the suture feeding channel 32, thereby allowing the suture 17 to be unwound from the reel 33 along any point of a circumference of the fastening assembly 4.

In accordance with an embodiment, the fastening assembly 4 comprises a side wall 34 which develops circumferentially about a longitudinal axis X. The fastening cavity 5 is formed in the side wall 34 and has a circumferential extension with respect to the axis X and a longitudinal axial extension parallel to the axis X, wherein the circumferential extension is preferably smaller than the axial extension. The fastening cavity 5 is delimited by a first sewing surface 10 and an opposite second sewing surface 12 which define a needle outlet aperture 35 (in the first sewing surface 10) and an opposite needle inlet aperture 36 (in the second sewing surface 12). The first and second sewing surfaces 10, 12 may be planar and parallel to the longitudinal axis X and may define planes which are radially oriented with respect to the longitudinal axis X. The needle path 28 may be circular and may extend coaxially and perpendicular to the longitudinal axis X of the fastening assembly 4, whereas the disentangling space 29 may be provided as an internally open disc-shaped empty space which encloses the needle path 28 and which is externally delimited and partially closed by the side wall 34 of the fastening assembly 4. The disentangling space 29 intersects the first and second sewing surfaces 10, 12 and the fastening cavity 5 at the needle outlet aperture 35 and needle inlet aperture 36.

The suture feeding channel 32 can be formed in the side wall 34 separate and at a distance from the fastening cavity 5, thereby preventing the end of the suture which is fed out of the feeding channel 32 to become entangled with the suture end secured to the needle 30. The suture feeding channel 32 may have a substantially circular shape and extend perpendicular to the longitudinal axis X around a circumference of the side wall 34.

In this embodiment, the suction apertures 8 may be formed in the sewing surfaces 10, 12 or, alternatively, the suction apertures 8 may open in the disentangling space 29 which is in communication with the fastening cavity 5.

Also, the opposing sewing surfaces 10, 12 may be movable towards each other by a moving mechanism 37. In accordance with an embodiment (FIGS. 12, 13) the opposing sewing surfaces 10, 12 are formed on two jaws 38 which are movable towards each other and away from each other for clamping the acquired tissue portion 6 and lining 2 before passing the needle 30 through them, and for releasing the tissue portion and lining after the passage of the needle 30.

Figure 12:
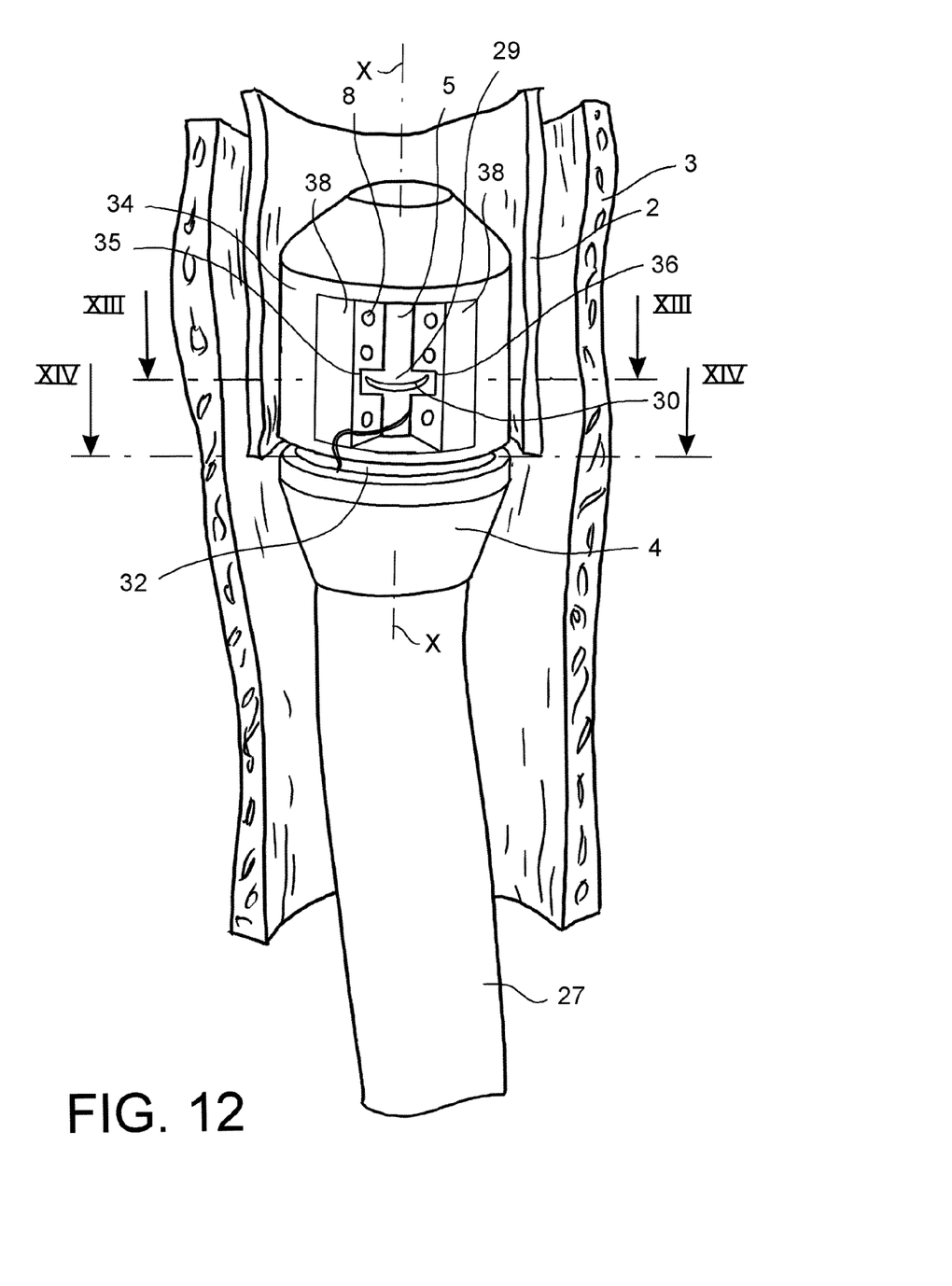
FIG. 12 illustrates an endoluminal applier for securing a tubular lining to a hollow organ in accordance with a further embodiment.

In the exemplary embodiment of FIG. 12, the jaws 38 are rotatable about an axis parallel to the longitudinal axis X or about the longitudinal axis X in order to improve the compatibility of the jaw movement and the circular needle path 28.

For the purpose of releasing the sutured tissue portion 6 and lining 2 from the fastening cavity, a pushing fluid, e.g. air or $CO_2$ or saline solution may be pumped through (a suction line connected with) the suction apertures 8 into the fastening cavity 5 or through a separate fluid feeding line with apertures opening into the fastening cavity 5. Also for the purpose of deploying and or unfolding the lining 2, a pushing fluid, e.g. air or $CO_2$ or saline solution may be pumped through (a suction line connected with) the suction apertures 8 into the fastening cavity 5 or through a separate fluid feeding line with apertures opening into the fastening cavity 5.

The needle drive assembly 31 is adapted to move the needle 30 along the needle path 28, release the needle 30 after having pushed the needle 30 out of the needle outlet aperture 35 into the fastening cavity 5, and catch the needle 30 when it enters the needle inlet aperture 36. For this purpose the needle drive assembly 31 may comprise a plurality of rotatable toothed gear wheels 39 or toothed sliders arranged along the needle path 28, but outside the disentangling space 29, and engaging a toothed surface 40 of the needle 30. The needle 30 itself may have a guide portion 41 which slidingly engages a guide 42 extending along the needle path 28 and adapted to guide and stabilize the needle 30 during its movement along the needle path 28.

In accordance with a yet further embodiment (FIGS. 16, 17, 18), the fastening assembly 4 forms a plurality of fastening cavities 5 arranged along a circumference of the fastening assembly 4 and a continuous annular needle path 28 which crosses all fastening cavities 5 and which extends inside a continuously radially externally open annular sewing groove 43 formed along a circumference of the fastening assembly 4. The stitching mechanism 9 comprises a needle 30 and a needle drive assembly 31 arranged for movement of the needle 30 along the needle path 28. A suture 17 is secured to the needle 30 and extends from the needle 30 inside the annular sewing groove 43, so that the needle 30 can repeatedly move along the entire needle path 28 (FIG. 17) and the resulting loop of suture 17 can be moved radially out of the sewing groove 43 (FIG. 18).

This embodiment allows to contemporaneously acquire a plurality of tissue portions 6 and lining portions along a circumference around the fastening assembly 4, then sending the needle 30 successively through all acquired tissue and lining portions, thereby obtaining a running purse string suture between the lining 2 and the tissue of the hollow organ 3, and eventually releasing the purse string sutured tissue and lining from the applier 1.

In accordance with an embodiment, a suture feeder, e.g. a reel 33 of suture may be arranged inside the fastening assembly 4 and adapted to release the suture 17 through a feeding channel 32 which opens into the sewing groove 43, preferably near a needle outlet aperture 35 at one of the fastening cavities 5. In this way the needle 30 can be sent one or more times along the entire annular needle path 28 and through the acquired tissue and lining portions, while the required suture 17 is fed through the feeding channel 32 near a first entrance point of the suture 17 in the tissue and lining.

Figure 13:
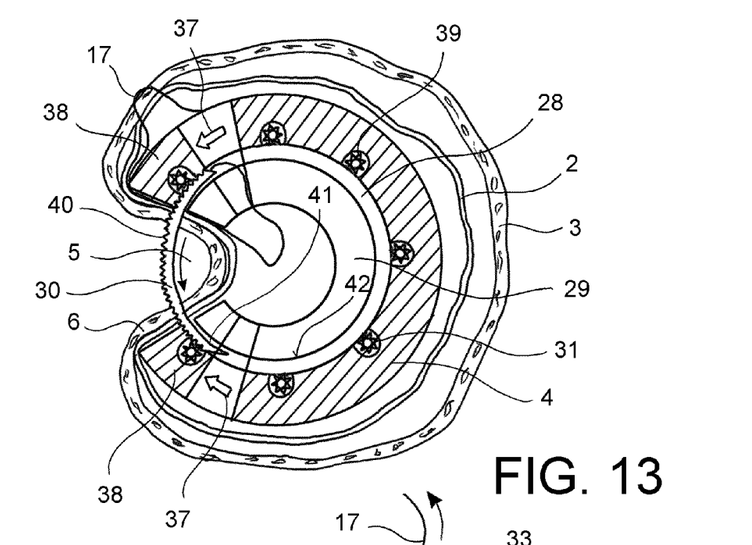
FIG. 13 is a sectional view in plane XIII-XIII in FIG. 12.
Figure 13A:
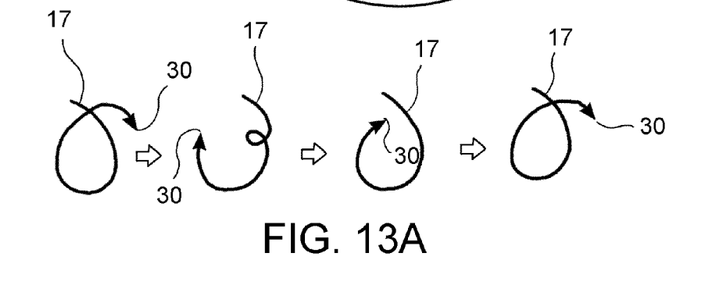
FIG. 13A illustrates a sequence of an open loop suture disentangling implemented by the applier of FIG. 12.
Figure 14:
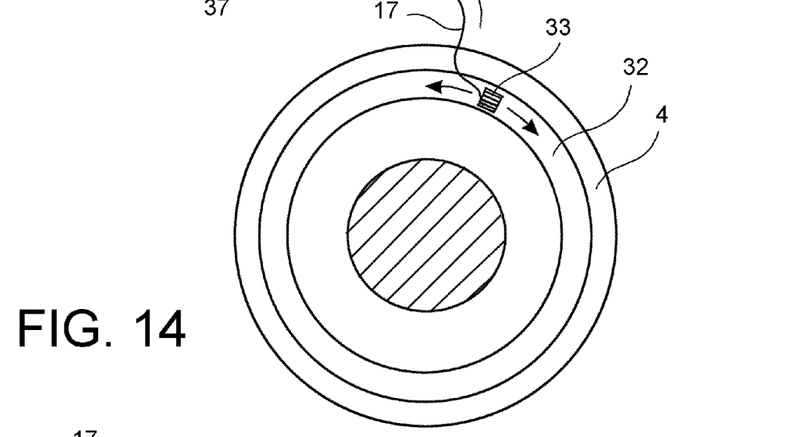
FIG. 14 is sectional view in plane XIV-XIV in FIG. 12.

Similar to the embodiment of FIGS. 12 to 14, also in the embodiment of FIGS. 16 to 18 the fastening assembly 4 may comprise a side wall 34 which develops circumferentially about a longitudinal axis X. The fastening cavities 5 are formed in the side wall 34 and have each a circumferential extension with respect to the axis X and a longitudinal axial extension parallel to the axis X, wherein the circumferential extension is preferably smaller than the axial extension. Each fastening cavity 5 can be delimited by a first sewing surface 10 and an opposite second sewing surface 12 which define a needle outlet aperture 35 (in the first sewing surface 10) and an opposite needle inlet aperture 36 (in the second sewing surface 12). The first and second sewing surfaces 10, 12 may be planar and parallel to the longitudinal axis X and may define planes which are radially oriented with respect to the longitudinal axis X. The needle path 28 may be circular and may extend coaxially and perpendicular to the longitudinal axis X of the fastening assembly 4, whereas the sewing groove 43 may be provided as an externally open ring groove which encloses the needle path 28 and which intersects the sewing surfaces 10, 12 and the fastening cavity 5 at the needle outlet apertures 35 and needle inlet apertures 36.

Also in this embodiment, the suction apertures 8 may be formed in the sewing surfaces 10, 12 or, alternatively, the suction apertures 8 may open into the fastening cavities 5 from a radially internal side of the fastening cavities 5, as illustrated in FIGS. 16 and 17.

Also, the opposing sewing surfaces 10, 12 may be movable towards each other by a moving mechanism 37. In accordance with an embodiment the opposing sewing surfaces 10, 12 are formed on two jaws 38 which are movable towards each other and away from each other for clamping the acquired tissue portions 6 and lining 2 before suturing, and for releasing the tissue portions and lining after completion of the suture.

In the exemplary embodiment of FIG. 16, the jaws 38 are rotatable about an axis parallel to the longitudinal axis X or about the longitudinal axis X in order to improve the compatibility of the jaw movement and the circular needle path 28.

For the purpose of releasing the sutured tissue portion 6 and lining 2 from the fastening cavities, a pushing fluid, e.g. air or $CO_2$ or saline solution may be pumped through (a suction line connected with) the suction apertures 8 into the fastening cavities 5 or through a separate fluid feeding line with apertures opening into the fastening cavities 5.

Alternatively or additionally, the fastening assembly 4 may be radially expandable and/or retractable in a manner to stretch the suture circumferentially (while feeding suture into the stretching zone to avoid rupture of the suture) and/or to withdraw radially from the released sutured tissue and lining. A radially expansion of the fastening assembly can be e.g. obtained through a wedge mechanism adapted to drive a e.g. conical wedge slider between a plurality of circumferentially arranged expansion segments 44 of the fastening assembly 4.

The needle drive assembly 31 is adapted to move the needle 30 along the needle path 28, release the needle 30 after having pushed the needle 30 out of the needle outlet aperture 35 into the fastening cavity 5, and catch the needle 30 when it enters the needle inlet aperture 36. For this purpose the needle drive assembly 31 may comprise a plurality of rotatable toothed gear wheels 39 or toothed sliders arranged along the needle path 28 and meshing with a toothed surface 40 of the needle 30. The needle 30 itself may have a guide portion 41 which slidingly engages a guide 42 extending along the needle path 28 and adapted to guide and stabilize the needle 30 during its movement along the needle path 28.

In order not to hinder the removal of the applier 1 from the sutured tissue and lining, the length of the needle 30 may be such that the needle 30 can be stopped within at least one section of the fastening assembly 4 without protruding into a fastening cavity 5. Alternatively, after releasing some of the tissue and lining portions from some of the fastening cavities 5 the needle 30 may be moved partially into an emptied fastening cavity 5, thereby withdrawing from a previously partially occupied neighboring fastening cavity 5.

Figure 19:
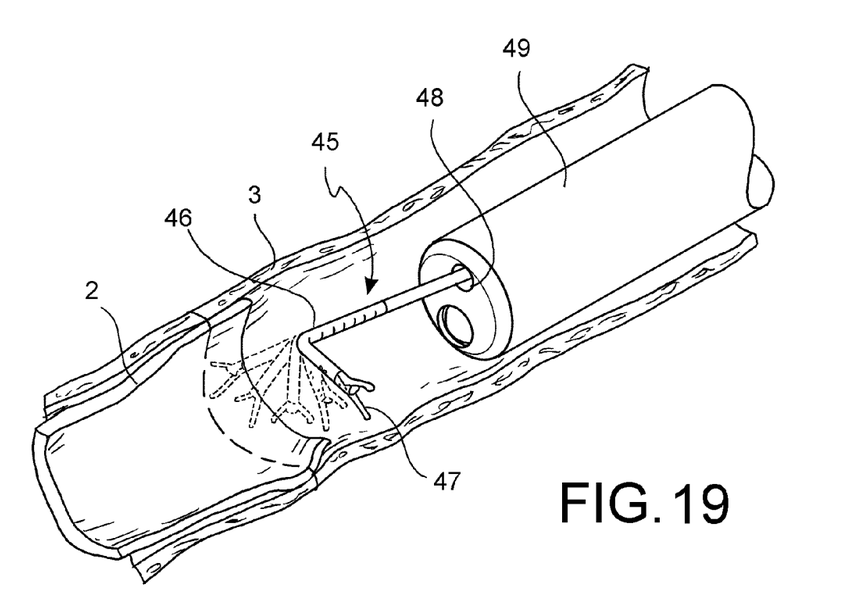
FIGS. 19 and 20 illustrate further devices and methods for endoluminally securing a lining inside a GI tract.

FIG. 19 illustrates a yet further method and device for securing a lining inside a hollow organ. A flexible endoluminal suturing device 45 with a rotatable and steerable shaft 46 and a distal clip applier 47 can be advanced through an instrument channel 48 of an endoscope 49 and is adapted to secure a lining in any desired section of the GI tract, e.g. at the esophagus, pylorus or duodenum. The clipping or suturing technique implemented by the device 45 may comprise also clipping and suturing techniques known from laparoscopic suturing devices. Thanks to the steerable shaft 46, the device can comfortably apply a suture or clip along a 360° circumference of lumen and lining. Specifically, a flexible endoscope is transorally inserted through the mouth and esophagus into the stomach and from the stomach further through the pylorus into the duodenum up to a target section of small intestine to which the lining is intended to be secured. The lining is transported to the target section of intestine by the endoscope. For instance, the lining may be inserted over a distal portion of the endoscope and released (e.g. pushed distally away) from the endoscope after the latter has reached the target section of intestine. Alternatively, the lining may be fed through an instrument channel of the endoscope and expelled from the instrument channel at the distal end of the endoscope. After positioning a proximal anchoring portion of the lining within the target section of intestine, the flexible suturing device 45 with the rotatable and steerable shaft 46 and the distal clip applier 47 is passed through the instrument channel of the endoscope so that a rotatable and steerable distal end portion of the shaft 46 with the clip applier 47 protrudes outside the endoscope. Then the shaft 46 is bent laterally so that the clip applier 47 can engage the lining and the surrounding intestinal wall in a first securing point. By activating the clip applier 47, the lining is secured to the intestinal wall in said first securing point. Subsequently, the clip applier 47 is recharged and prepared for the application of a further clip or suture. The rotatable and steerable shaft 46 is then rotated at a suitable angular pitch with respect to the first securing point and bent laterally (radially outward) to engage the lining and the surrounding tissue in a further securing point. The clip applier is again activated to apply a second clip or suture to the lining and tissue, thereby securing the lining also in the further securing point. The procedure can be repeated until the lining is secured to the surrounding tissue in a plurality of securing points along a circumference of the lining. After completion of the anchoring step, the distal end portion of the shaft is straightened and proximally withdrawn into the instrument channel of the endoscope. Then the entire suturing device 45 is withdrawn through the instrument channel of the endoscope and out of the patient's body.

Figure 20:
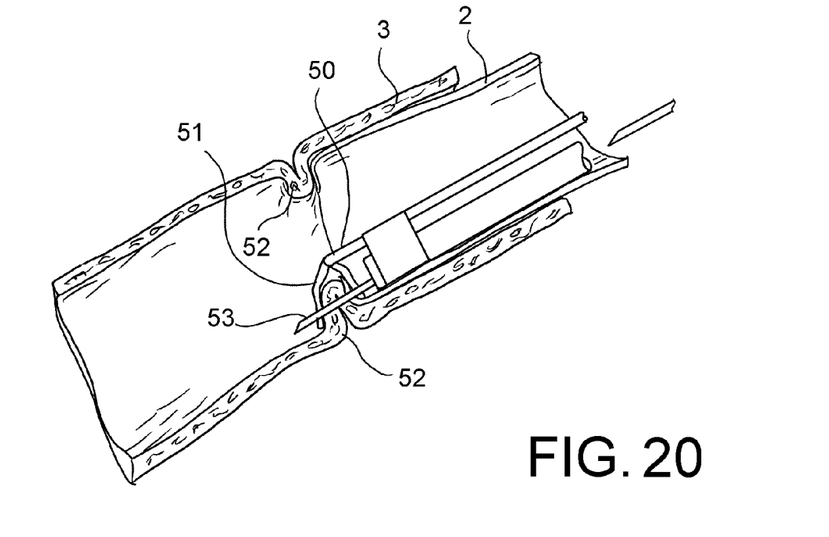

FIG. 20 illustrates a yet further method and device for securing a lining inside a hollow organ. A flexible endoluminal grasping device 50 with a grasper 51 adapted to create small folds 52 of tissue and lining is combined with a suturing device 53 adapted to apply a T-tag or to stitch a needle 30 with a suture thread 17 through the fold 52. Also in this case the combined device is rotatable to reach any desirable position along a 360° perimeter of tissue lumen and lining.

The lining 2 intended to form an endoluminal bypass conduit may be formed of any suitable biocompatible graft material such as polyester or PTFE, rubber, Teflon, Nylon, Dacron, polyethylene, polystyrene, polyurethane, polyethylene terephtalate, etc. In accordance with a further embodiment, both the lining 2 and the running suture could be bioabsorbable and adapted to completely dissolve over time.

Although preferred embodiments of the invention have been described in detail, it is not the intention of the applicant to limit the scope of the claims to such particular embodiments, but to cover all modifications and alternative constructions falling within the scope of the invention.

The invention claimed is:

1. An endoluminal applier for anchoring a tubular lining to a hollow organ, the applier comprising:
   a fastening assembly forming a fastening cavity configured to receive a tissue portion of the hollow organ together with a portion of the lining; wherein the fastening assembly forms a continuous annular needle path which crosses the fastening cavity and which is formed inside an unobstructed disentangling space inside the fastening assembly, wherein the stitching mechanism comprises a needle and needle drive assembly arranged for movement of the needle along the needle path, and wherein a suture is secured to the needle and extends from the needle through the disentangling space and through the fastening cavity outside the fastening assembly, so that the needle can repeatedly move along the entire needle path without winding the suture around any part of the fastening assembly;
   wherein the fastening assembly comprises an externally continuously open annular suture feeding channel extending all around the fastening assembly and a suture feeder adapted for feeding the suture from inside the suture feeding channel at any point along the suture feeding channel;
   a suction device having one or more suction apertures opening into the fastening cavity for acquiring the tissue portion and lining into the fastening cavity; and
   a stitching mechanism configured to stitch into the fastening cavity and to apply a running suture to the tissue portion and lining.

2. The endoluminal applier of claim 1, wherein the suture feeding channel is formed separate and at a distance from the fastening cavity.

3. The endoluminal applier of claim 1, wherein the needle path is circular and extends coaxially to a longitudinal axis, and the disentangling space is an internally open disc-shaped empty space which encloses the needle path and intersects the fastening cavity.

4. The endoluminal applier of claim 1, wherein the fastening assembly comprises a side wall that extends circumferentially about a longitudinal axis of the endoluminal applier and one or more fastening cavities are formed in the side wall and have each a circumferential extension with respect to the axis and a longitudinal axial extension parallel to the longitudinal axis, said circumferential extension being smaller than said axial extension.

5. The endoluminal applier of claim 1, wherein one or more fastening cavities are each delimited by a first sewing surface forming a needle outlet aperture and an opposite second sewing surface forming a needle inlet aperture, the fastening assembly being configured to move the first and second sewing surfaces towards each other.

6. The endoluminal applier of claim 1, in which the suction device is configured for a push fluid to be pumped through the suction apertures into the fastening cavity.

7. An endoluminal applier for anchoring a tubular lining to a hollow organ, the applier comprising:
   a fastening assembly forming a fastening cavity configured to receive a tissue portion of the hollow organ together with a portion of the lining, the fastening assembly having an externally continuously open annular suture feeding channel extending all around the fastening assembly and a suture feeder adapted for feeding a suture from inside the suture feeding channel at any point along the suture feeding channel;
   a suction device having one or more suction apertures opening into the fastening cavity for acquiring the tissue portion and lining into the fastening cavity; and
   a needle and a needle drive assembly configured to stitch into the fastening cavity and to apply a running suture to the acquired tissue portion and lining.

8. The endoluminal applier of claim 7, wherein the suture feeding channel is formed separate and at a distance from the fastening cavity.

9. The endoluminal applier of claim 7, wherein the fastening assembly forms a continuous annular needle path that crosses the fastening cavity and that is formed inside an unobstructed disentangling space inside the fastening assembly, wherein the needle drive assembly is arranged for movement of the needle along the needle path, and wherein a suture is secured to the needle and extends from the needle through the disentangling space and through the fastening cavity outside the fastening assembly.

* * * * *